US006236708B1

United States Patent
Lin et al.

(10) Patent No.: US 6,236,708 B1
(45) Date of Patent: May 22, 2001

(54) 2D AND 3D TOMOGRAPHIC X-RAY IMAGING USING FLAT PANEL DETECTORS

(75) Inventors: Zhongmin Lin, Twinsburg; Donald E. Negrelli, Gates Mills; Leonard F. Plut, Mentor; Jerome J. Griesmer, Kirtland, all of OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/200,652

(22) Filed: Nov. 25, 1998

(51) Int. Cl.$^7$ .................................................. G01N 23/00
(52) U.S. Cl. .............................................................. 378/22
(58) Field of Search ................................ 378/22, 21, 98.8

(56) References Cited

U.S. PATENT DOCUMENTS

| | | | |
|---|---|---|---|
| 4,139,776 | * 2/1979 | Hellstrom | 378/22 |
| 4,630,296 | 12/1986 | Haaker et al. | 378/2 |
| 5,812,191 | * 9/1998 | Orava et al. | 378/98.8 |
| 5,978,440 | * 11/1999 | Kang et al. | 378/21 |

FOREIGN PATENT DOCUMENTS

| | | |
|---|---|---|
| 2746035A1 | 4/1979 | (DE) . |
| 0106402A2 | 4/1984 | (EP) . |
| 2046468 | 11/1980 | (GB) . |
| 2062403 | 5/1981 | (GB) . |
| 2063509 | 6/1981 | (GB) . |

\* cited by examiner

Primary Examiner—Craig E. Church
(74) Attorney, Agent, or Firm—Fay, Sharpe, Fagan, Minnich & McKee, LLP

(57) ABSTRACT

A penetrating radiation source (14) is disposed on one side of a object (10) which is on a object support (12). A flat panel radiation detector (18) is stationarily disposed on the opposite side of the object (10) than the source (14). A moving system (16, 50, 52) moves the source (14) with respect to the object (10). In each position $(X_i, Y_i, Z_i)$ of the source (14) a center ray of the x-ray beam strikes the detector (18) at a corresponding location $(x_i, y_i, 0)$. For each position $(X_i, Y_i, Z_i)$ of the source (14), the image $(x_i, y_i, 0)$ of an object located on a focal plane offsets by a vector displacement $(D_i)$ relative to a reference position $(x_o, y_o, z_o)$ of the image when the source is at $(X_0, Y_0, Z_0)$. A processor (28) shifts and interpolates each view by the different vector displacements corresponding to each of the focal planes $(L_1, L_2, \ldots)$ and integrates the images to generate a series of slice image representations which are stored in a volume image memory (30). In this manner, by adjusting the view offset by an amount corresponding to each of the focal planes, $(L_1, L_2, \ldots)$ the same data set is used to generate all of the slices of the resultant volume image.

14 Claims, 7 Drawing Sheets

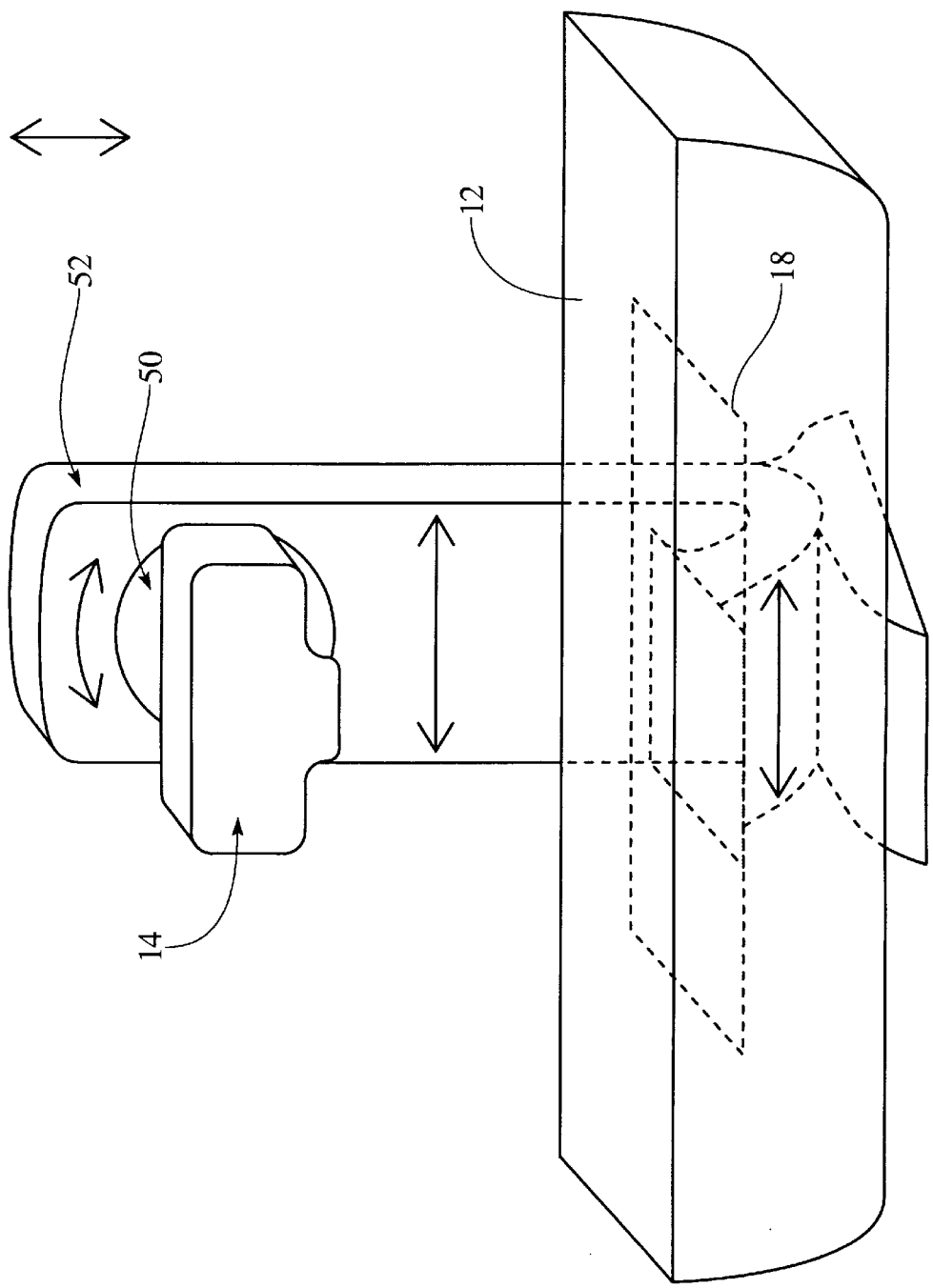

2D AND 3D TOMOGRAPHIC X-RAY IMAGING USING FLAT PANEL DETECTORS

BACKGROUND OF THE INVENTION

The present invention relates to the art of tomographic imaging. It finds more particular application in 3D and 2D tomographic imaging based on one or more layers in a human body being measured by an x-ray system. However, it will be appreciated that the invention has other applications such as imaging of an object with other types of penetrating radiation to determine the make up and constituent components of that object and it may be advantageously employed in other environments and applications.

Traditionally, x-rays are projected from an x-ray source and through an object for exposing an image onto x-ray film. The image is typically a compression of all of the structures in the imaged portion of the body exposed onto the x-ray film. The vast amount of superimposed information can make diagnosis difficult.

In one technique for emphasizing a selected plane of the object, the x-ray source and the x-ray film move contra-cyclically in parallel planes which are parallel to the plane of interest. More specifically, the x-ray source and the x-ray film are moved such that the ray which exposes each incremental element of the x-ray film pivots about a fixed point in the plane of interest or focal plane. In this manner, each incremental element of the x-ray film is consistently exposed by radiation passing through a constant point in the focal plane. However, because the ray is pivoting about the constant point, the same increment of x-ray film is also exposed by a variety of structures outside the focal plane. In this manner, information from structures outside of the focal plane become blurred on the same x-ray film on which image data attributable to structures on the focal plane remains sharp and crisp.

If the diagnostician wishes to view another selected plane, the position of the patient is shifted relative to the x-ray source and the x-ray film canister such that the focal plane passes through a different selected plane of the object. With sufficient time, a series of parallel planer film images can be generated through the object. However, because each image takes a significant amount of time to generate, there is a significant temporal offset or time evolution among the images.

The temporal offset can be greatly reduced with volumetric CT scanners. However, CT scanners are not only much larger and more complex then the traditional x-ray film imaging systems, they are also much more expensive. Moreover, CT scanners are a different piece of equipment often positioned in a different room or location within the facility and in some instances at a different facility completely. Typically, the CT scanners are operated by different technicians. Accordingly, there are time delays in transporting the patient from one piece of equipment to the other, sometimes involving the making of additional appointments. Thus, the film images and the CT images may have very large temporal offsets. Moreover, it is difficult to maintain the position and orientation of the patient constant during such transporting. Accordingly, the resultant CT images are often not of the same physiology as the film images.

The present invention contemplates a new and improved apparatus and method which overcomes the above-referenced problems and others.

SUMMARY OF THE INVENTION

In accordance with the present invention, a device for imaging an object generates a multi-dimensional image of the object. The device includes a movable light source for sending a radiation beam through the object. A detector detects the radiation beam after it has passed through the object and generates electronic data representative of the detected radiation intensity. A system non-linearly displaces the radiation source relative to the object during the imaging. A processor receives, sorts, and processes the data to generate a series of stacked planar images of the object, each of which has minimized blurring in a corresponding plane and enhanced blurring outside of the corresponding plane.

In accordance with a more limited aspect of the present invention, the x-ray source moves in an arc to minimize magnification distortion by aligning the center of the cone beam with the region of interest.

In accordance with another more limited aspect of the present invention, the radiation source moves transversely to and along the arc to enhance off-plane blurring.

In accordance with another more limited aspect of the present invention, the radiation source is movably mounted below the object and a flat panel detector is located above the object in a stationary position.

In accordance with a more limited aspect of the present invention, the radiation source and the detector are located on opposite sides of an object support. The gantry moves the x-ray source up and down and left to right in relation to a flat panel detector.

A first advantage of the present invention is that it concurrently generates data for processing a plurality of layers.

Another advantage of the present invention resides in a reconstruction technique which quickly and easily reconstructs 2D and 3D tomographic images.

Another advantage is that electronic image representations are generated.

Yet another advantage is that the imaged planes can be changed after the data collection process is complete.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 6 shows a side-view of a tomographic imaging system according to a third embodiment of the invention;

DETAILED DESCRIPTION OF THE PREFERRED EMBODIMENTS

Figure 1:
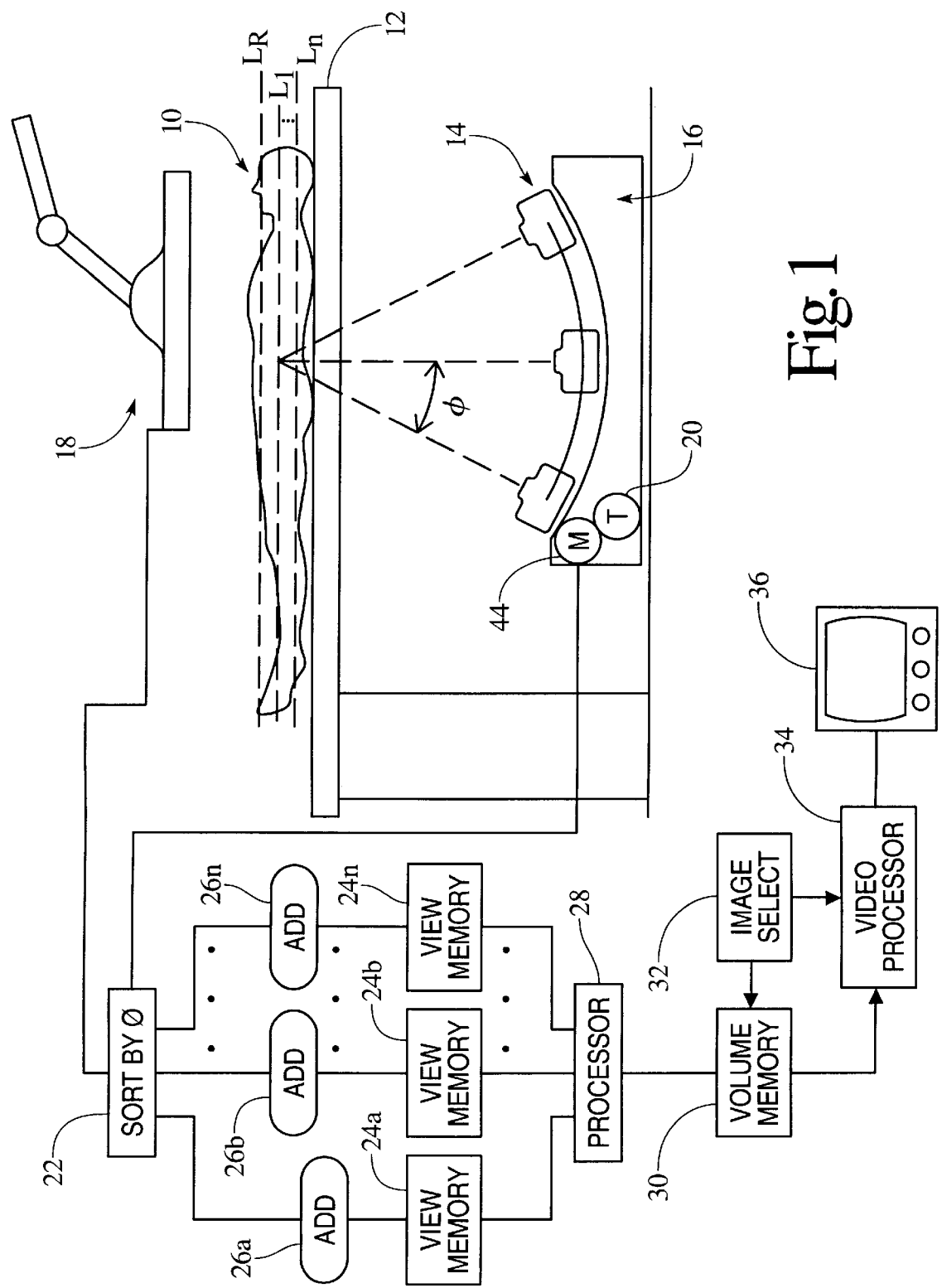
FIG. 1 illustrates a diagrammatic side-view of a first embodiment of the present invention.

With reference to FIG. 1, an object 10, preferably a subject or patient, is supported on an x-ray table 12 or other support surface. An x-ray tube or other radiation source 14 is mounted below the table 12 on an x-ray source moving system 16. The x-ray source moving system 16 moves the x-ray source 14 back and forth along a arc of constant radius with respect to the object 10. A flat panel, solid state radiation detector 18 is disposed above the table 12 in alignment with an x-ray beam projected by the x-ray source 14. In the preferred embodiment, the flat paneled detector 18 is a rectangular grid of radiation sensitive elements, each of which generates an electrical signal indicative of an intensity or amount of received radiation.

As a radiation source 14 moves below the object 10, the elements of the flat panel detector 18 are periodically sampled. More specifically, an x-ray source position detector 20 monitors an angular position φ of the x-ray source 14 by monitoring its physical position along the x-ray moving system 16. The flat paneled detector 18 is read out at each of a plurality of preselected angular positions as the x-ray source 14 moves back and forth along the arc. The x-ray source 14 can be stepped incrementally for optimal precision. Alternatively, the x-ray source 14 can be moved continually with sampling occurring over a short arc with minimal image degradation.

A sorting routine 22 receives the sampled period of image data or view at each of the angular positions and stores it in a corresponding view memory $24a$, $24b$, ..., $24n$. In the preferred embodiment in which the x-ray source moves back and forth a plurality of times, a series of view adders $26a$, $26b$, ..., $26n$ add each new view from a corresponding angular position to the views already in the corresponding view memory in order to sum or average the plurality of collected views.

As described in greater detail below, a processor 28 processes views from the view memories $24a, 24b, ..., 24n$. As explained in greater detail below, each of the views is offset and summed with preceded views in such a manner that radiation attenuation attributable to portions of the object in a first focal plane $L_1$ are coherent and have minimal blurring while radiation attenuation from portions of the object 10 outside of the first focal plane $L_1$ have maximum blurring. In this manner, a first slice of volumetric image data is generated and stored in a volumetric image memory 30. Changing the offset and summing as described in detail below, data representative of a second focal plane $L_2$ and plurality of subsequent focal planes $L_n$ are generated and stored in the volumetric image memory 30. It is to be appreciated, that as long as the views are stored in the view memories $24a, 24b, ..., 24n$ the offsets can be reselected to select a different array of focal planes $L_1, L_2, ..., L_n$ which might better illustrate a region of interest.

An operator controls an image selection processor 32 which selects the image to be displayed. Typical images include a single slice through a region of interest, coordinated sagittal, coronal, and transverse slices through the region of interest, oblique slices, volumetric renderings, and the like. The image selection processor 32 causes the appropriate values to be read out of the volumetric image memory 30 to a video processor 34 which converts the data into appropriate format for display on a video monitor or other human readable display 36.

Figure 2C:
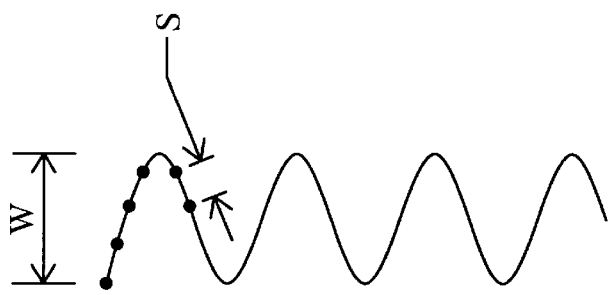
FIG. 2C illustrates a cosine or sine radiation source motion path.
Figure 2A:
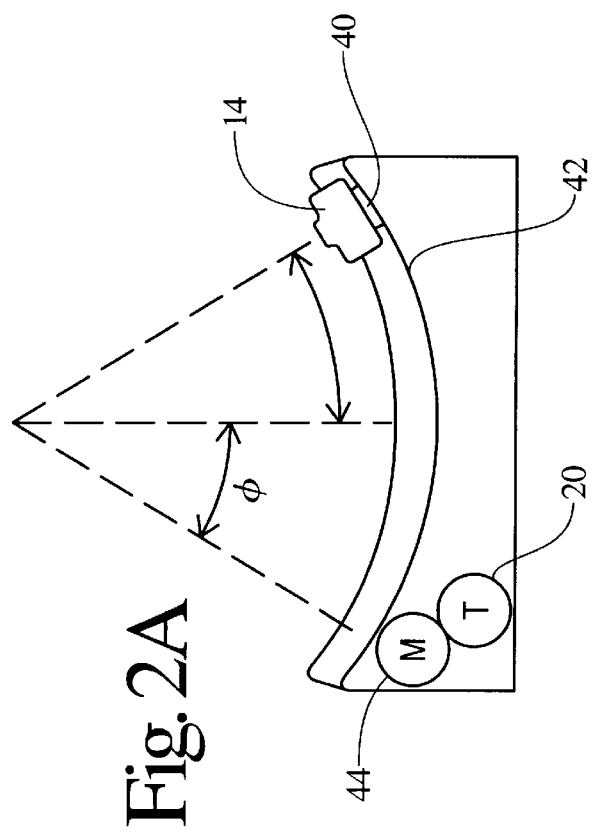
FIG. 2A is a perspective view illustrating the motion of an x-ray source.
Figure 2B:
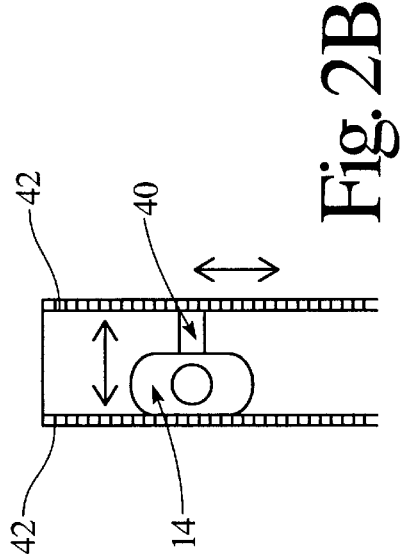
FIG. 2B illustrates a top view of an x-ray source track of FIG. 2A.

With reference to FIGS. 2A, 2B, and 2C, the under-table x-ray tube 14 moves along the arcuate trajectory with a motion that combines two degrees of freedom. In particular, the motion of the x-ray source 14 has components which are both parallel and transverse to a longitudinal-vertical plane, but symmetrical through the object as the overhead flat panel 18 remains stationary. To this end, the x-ray source movement system 16 includes a transverse slide bar or support 40 which is mounted on its edge to a pair of similar rails 42 which extend along the sides of the arcuate path. The x-ray source moving system 16 includes a first drive, such as a motor 44, and drive train for moving the slide bar 40 along the track 42. As indicated above, the motor 44 can be a stepper motor for moving the x-ray source 14 in fixed increments or a synchronous or servo motor for moving it at a controlled speed. The encoder 20 for indicating the angular position of the source 14 can conveniently be a tachometer. The slide bar 40 carries a second drive (not shown) for moving the x-ray source 14 transversely relative to the vertical-longitudinally plane.

A motor control controls the two drives such that the radiation source 14 follows a preselected trajectory, such as the sinusoidal trajectory illustrated in FIG. 2C. Other, more complex motions are also contemplated such as spiral, circular, elliptical, or hypcycloidial. In the illustrated sinusoidal embodiment, the radiation source trajectory has a width W and a sampling interval S, both of which are controllable.

During the tomographic procedure, a set of digital photo-spot or pulsed fluoroscopic images or views is acquired and stored. The image set is then processed by the 3D tomographic image reconstruction processor 28 to create 2D tomographic images which are stacked to form the 3D tomographic image. The magnification of the imaging geometry of the system is not constant so a distortion correction of the varied magnification is employed to suppress the image blurring and to increase the image visibility. This is described hereinafter with reference to FIG. 9 below.

It is to be appreciated that the system can also be configured for conventional radiographic and fluoroscopic applications. During the radiographic applications, the x-ray tube 14 is positioned in the middle of the track 42.

The use of the flat panel detector 18 offers higher dynamic range than that of the conventional screen film. During one tomographic procedure, a set of digital flat panel images is acquired. From this set of flat panel images, multi-layer tomographic images of the anatomy of the object 10 are constructed. A 3D tomographic image is constructed from this same set of images. The processor 28 uses digital processing for image enhancement and distortion correction to increase image contrast and visibility. The control system is simple. The two motors, one for the motion along the track and one for moving the x-ray source along the slide bar 40, along the trajectory of FIG. 2C. This design makes the motion control easier and reliable.

Turning now to the second embodiment shown in FIGS. 3–5, x-ray source 14 is mounted overhead and the flat panel detector 18 is mounted below the object 10 disposed on the x-ray table 12. The x-ray source 14 moves along transverse and longitudinal axes relative to the object 10.

Figure 4:
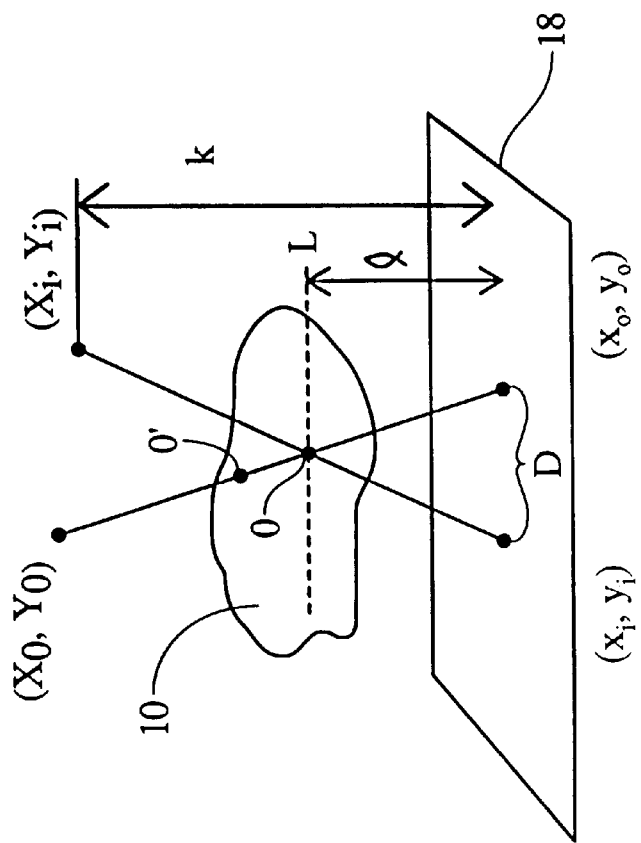
FIG. 4 is a pictorial representation illustrating a reconstruction algorithm used when the radiation source moves in 2 Dimensions.
Figure 3:
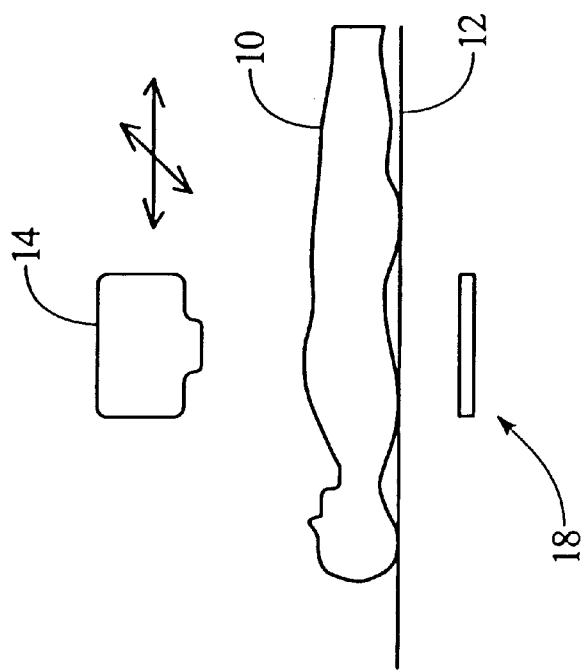
FIG. 3 is a diagrammatic illustration of a second embodiment of the invention.

With reference to FIGS. 3 and 4, a digital tomographic system with a fixed magnification is illustrated. This system has the simplest reconstruction algorithm since there is no vertical motion of the source in this example. The flat panel detector 18 is located under the object 10 and is stationary during the tomographic procedure. An overhead x-ray tube 14 moves across the region of interest of a patient 10. In the illustrated diagnostic procedure, the tube 14 moves parallel to the flat panel detector 18 such that the magnification remains constant. The processor 28 integrates the views to create a tomographic image of a selected focal plane L. The x-ray source 14 is kept at a constant distance k from the detector plane 18, where the focal plane L is at a constant distance (from the detector plane 18. To reconstruct an image of layer L, an initial x-ray source position $(X_o, Y_o)$ is selected as a reference position. The ray from point $(X_o, Y_o)$ through a selected element O in the focal plane L of the object 10 intersects the flat detector 18 at $(x_o, y_o)$. When the x-ray tube 14 moves from position $(X_o, Y_o)$ to position $(X_i, Y_i)$ the ray through element O in focal plane L, intersects the detector 18 at $(x_i, y_i)$. The displacement D between the position $(x_o, y_o)$ and $(x_i, y_i)$ is calculated by:

$$x_i = x_o + (1/(k-1))*(X_o - X_i) \quad (1a)$$

$$y_i = y_o + (1/(k-1))*(Y_o - Y_i) \quad (1b).$$

It is to be appreciated that an incremental element O which lies along the ray from $(X_o, Y_o)$ to $(x_o, y_o)$ also lies along the ray between $(X_i, Y_i)$ to $(x_i, y_i)$. Further, different incremental elements lie along these two rays. As the x-ray source 14 moves to additional positions, the only common incremental element of the additional rays is still the incremental element O. Although illustrated with respect to incremental element O, all incremental elements in the plane L are effected likewise. It will further be observed that those incremental elements such as O', which do not lie on plane L change their pixel location, i.e., the pixel which represents the radiation attenuation through such incremental element, in each view. In this manner, the contribution of the out of focal plane incremental elements to the summed image become blurred or homogenous with sufficient blurring, the out of plane incremental elements O' are reduced to a background noise, preferably merely a haze. Optionally, this haze can be reduced through filtering, such as reducing all gray scale values below a preselected or calculated level to a base background level, i.e., black.

The $(x_i, y_i)$ view is shifted by vector D and added to the $(x_o, y_o)$ view. This process is repeated for a multiplicity of x-ray source positions to build the image of the first focal plane L and the image of the object O can be enhanced by adding two images together. The images of any object point on layer L can be enhanced using the same method.

Figure 5:
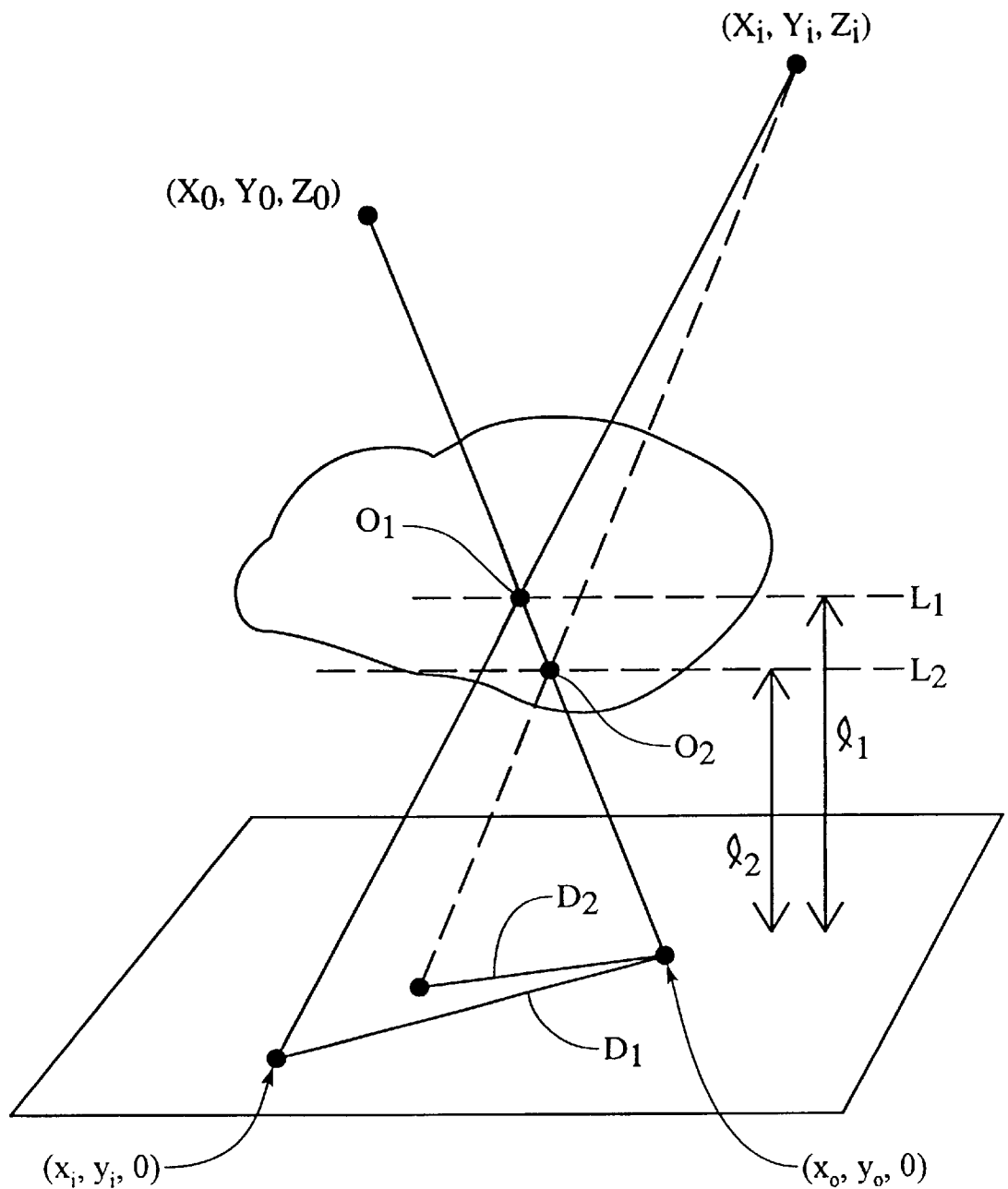
FIG. 5 is a pictorial representation illustrating a reconstruction algorithm used when the radiation source moves in 3 Dimensions.

With reference to FIG. 5, a more general case in which the magnification is not constant is shown. The x-ray source 14 moves from the initial or reference position $(X_o, Y_o, Z_o)$ from which an image falls at $(x_o, y_o, 0)$ on detector 18 after passing through the incremental element $O_1$, of focal plane $L_1$, while the distance $l_1$ between the flat panel detector 18 and the reconstruction layer $L_1$ remains constant. The x-ray source 14 moves from the initial or reference position $(X_o, Y_o, Z_o)$ to a first incremental position $(X_i, Y_i, Z_i)$ from which an image falls at $(x_i, y_i, 0)$ on detector 18 after passing through the incremental element $O_1$, of focal plane $L_1$, while the distance $l_1$ between the flat panel detector 18 and the reconstruction layer $L_1$ remains constant. When the x-ray source 14 moves along an arc of constant radius the z-component changes. The distance $l_1$ is held constant and the detector plane is arbitrarily set as $z_o = z_i = 0$. Equations (1a) and (1b) become in their dimensions:

$$x_i = x_o + (l_1/(Z_o - l_1))(X_o - X_i) \quad (2a)$$

$$y_i = y_o + (l_1/(Z_o - l_1))(Y_o - Y_i) \quad (2b)$$

$$z_i = 0 \quad (2c).$$

The position $(x_i, y_i, 0)$ is calculated for each point of the focal plane $L_1$, as:

$$x_i = [Z_i(Z_o - l_1)/Z_o(Z_i - l_1)]x_o + [(Z_i l_1/Z_o(Z_i - l_1)]*X_o - [l_1/(Z_i - l_1)]X_i \quad (3a)$$

$$y_i = [Z_i(Z_o - l_1)/Z_o(Z_i - l_1)]y_o + [(Z_i l_1/Z_o(Z_i - l_1)]*Y_o - [l_1/(Z_i - l_1)]Y_i \quad (3b)$$

$$z_i = 0 \quad (3c)$$

It should be appreciated that the ray from the x-ray source 14 at $(X_o, Y_o, Z_o)$ falling on a corresponding point $(x_o, y_o, 0)$ on the flat panel detector 18 passes through elements on a plurality of planes, including element $O_2$ of plane $L_2$. The ray from the x-ray source 14 at point $(X_i, Y_i, Z_i)$ passes through the element $O_2$ and strikes the detector plane 18 at a different point offset by the vector $D_2$ from point $(x_o, y_o, 0)$ By simply adjusting the offset vector $D_2$, the same series of views can be summed to generate images in each of a multiplicity of focal planes.

During a single volumetric tomographic imaging procedure, a single set of the digital views is collected in the view memories 24a, 24b, . . . , 24n. For a first plane $L_1$ which is a distance $l_1$ from the flat plate detector 18, the data value of each view is adjusted in accordance with Equations (3a) and (3b) to correct for the offset and magnification and the views are summed. Then, for a second focal plane, $L_2$ a distance $l_2$ from the detector plane 18, the same adjustments are again made and these are summed to generate a slice image for a second plane $L_2$. This same process of adjusting the magnification and offset adjustments to the same data are repeated until each of the planes of the volumetric image representation are generated. These steps can be repeated with smaller interfocal plane spacings to get greater detail in a separate region of particular interest.

During a volumetric tomographic imagery procedure, a set of digital views is acquired. From this set of flat panel views, multi-layer tomographic images of anatomy are constructed. A 3D or volumetric tomographic image is constructed by stacking additional slice images reconstructed from the same set of tomographic views. Digital processing is used for image enhancement and distortion correction to increase the image contrast and visibility.

Figure 7:
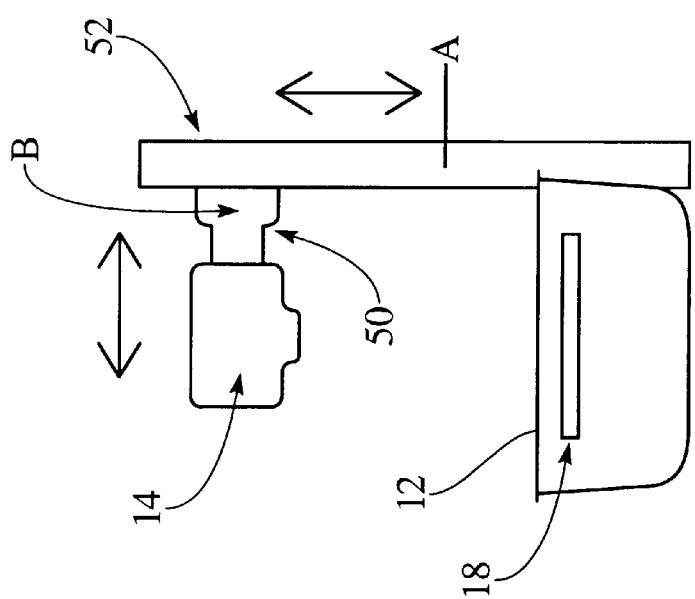
FIG. 7 shows an end view of the third embodiment of the present invention with the x-ray source extended.

Turning now to FIGS. 6 and 7, a third embodiment is shown where an x-ray tomographic system which has the x-ray source 14 attached to a rotatable gantry 50, which is, in turn, attached to a translating gantry 52. X-rays from the source 14 pass through the object 10 located on the x-ray table 12. The x-ray beam is detected by the flat panel detector 18 positioned below the table 12.

Figure 8:
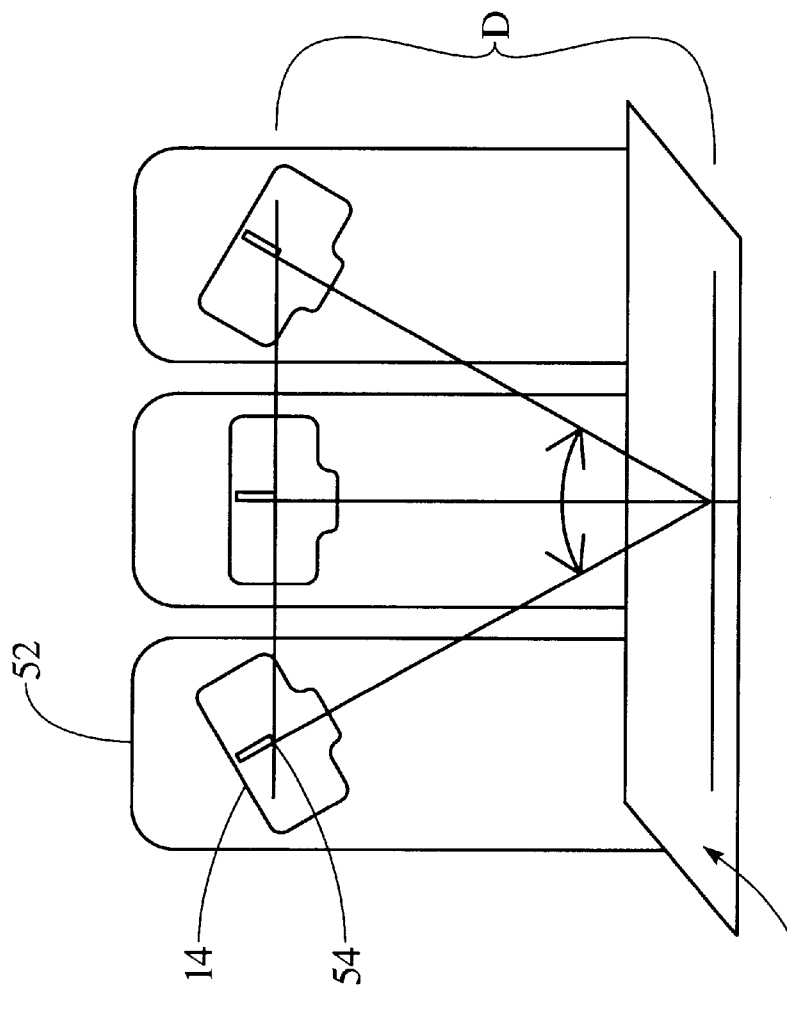
FIG. 8 shows the movement of the x-ray source according to the third embodiment of the present invention.

With reference to FIG. 8, the gantry 50 is rotated to align the flat panel detector 18 automatically with the overhead x-ray tube 14 during radiographic procedures. During the tomographic procedure, the overhead x-ray tube 14 is driven by servo or stepper motors (not shown) which allows it to scan relative to a region of interest of the object. The flat panel detector 18 remains stationary. The translation gantry 52 moves left and right while the rotational gantry 50 rotates counterclockwise and clockwise with respect to the translational gantry 52 to keep the collimated x-ray cone beam aligned with the region of interest.

With continuing reference to FIGS. 6–7, the rotating gantry 50 and the longitudinally translating gantry 52 are interconnected such that the x-ray tube 14 can move toward and away from the flat paneled detector 18. The position of the source point 54 is located on the rotation axis of the gantry 50. In this manner, the motions can be coordinated such that the focal spot of the x-ray tube 14 follows an arcuate trajectory that is equidistant from the flat paneled detector 18 at all locations to minimize magnification effects.

It is also to be appreciated, the rotating gantry 50 can also be configured to move inward and outward relative to the translating gantry 52. This enables the x-ray source 14 to move with both transverse and longitudinal components of motion relative to the object. As discussed above, the additional motional components causes the out of plane contributions of the image to be blurred more fully reducing the background contributions.

It is also to be appreciated that the object could be in a commercial warehouse environment and may be any object which needs to be measured for its constituent layer parts during processing. As another option, the surface that supports the object can move relative to the x-ray source, for example it could be a conveyor belt.

Figure 9:
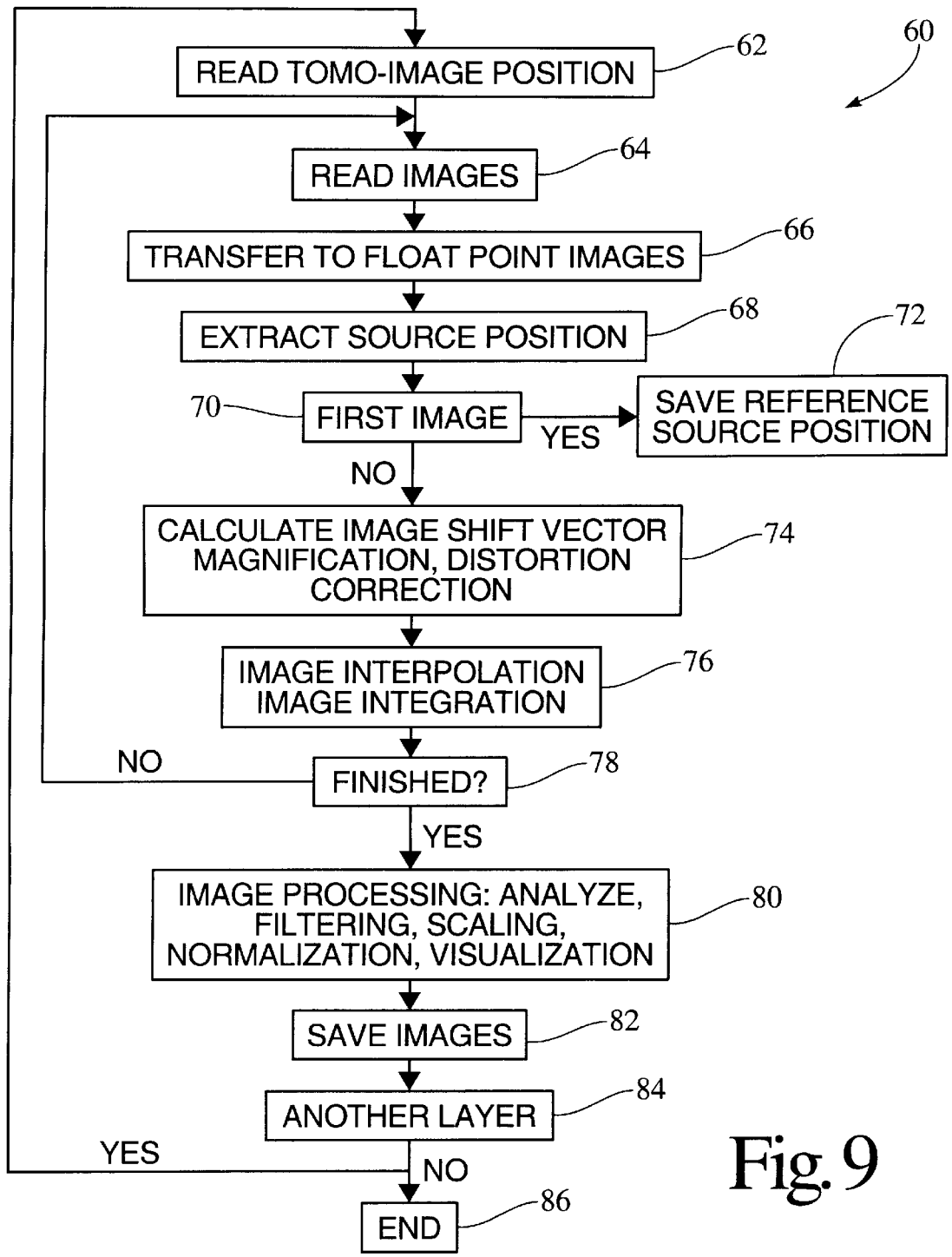
FIG. 9 shows a flow chart for determining and generating 2D and 3D tomographic images according to the several embodiments of the invention.

With reference to FIG. 9, there is a flow chart 60 detailing a preferred method for reconstructing the 2D and 3D tomographic image representations. At a step 62, the tomographic position of the selected slice is initially read. A step 64 reads out a view of an object from the detector 18 which a step 66 converts into a floating point view. Concurrently, a step 68 extracts an exact source position for the encoder 20. Next, a step 70 determines if this is the first view which was completed. If "yes", a step 72 saves the initial or reference source position. If this determination step 70 is "no", then a step 74 calculates the image shift vector D and the magnification errors as set forth in Equations (3a), (3b), (3c), a view summation or integration by which the step of 76 summed or integrated views build the resultant image. A step 78 determines if the system is finished detecting views for the current layer, i.e., whether the slice image is complete. If this determination in step 78 is "yes" then the slice image is reconstructed and image processing step 80 is performed.

First, the image processing step 80 performs image analysis of the image followed by a noise clipping and filtering to remove noise and blurred background, particularly contributions attributable to out of slice elements. The step 80 also performs scaling and normalization of the image to optimize the image for viewing.

Once these digital information processes are complete, the slice imaged (data is saved in a step 82) into the volume image memory 30 for later or immediate display. Further, a next layer determination step 84 determines whether this current image is the last slice of the volume to be reconstructed or, alternatively, whether there is another layer which is to be reconstructed and saved. If this determination is "yes", then the next slice or layer is selected in step 62 and steps 64–82 are repeated on the same views stored in view memories 24a, 24b, . . . 24n. If this determination is "no", then a step 86 ends the reconstruction process.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A tomographic imaging system comprising:
a support surface for stationarily supporting a region of interest of a patient to be imaged;
a flat panel detector stationarily mounted parallel to the patient support surface, the flat panel detector being larder than the region of interest in planes parallel to the patient support surface;
an x-ray source for generating penetrating radiation, the x-ray source being movably mounted on an opposite side of the region of interest from the flat panel detector such that the penetrating radiation from the x-ray source passes through the region of interest and is received by the flat panel detector;
a moving system for moving the x-ray source relative to the region of interest such that the penetrating radiation passing from the x-ray source to the flat panel detector passes through the region of interest at a plurality of angles and impinges upon a plurality of different portion of the flat panel detector, the flat panel detector being accessed to generate a plurality of views corresponding to each of a plurality of the angular orientations between the x-ray source and the region of interest;
a reconstruction processor for reconstructing the plurality of views into a tomographic image, the reconstruction processor including:
a means for sorting the views by the angle with which the radiation passed through the region of interest and spatially shifting the views in accordance with said angle;
a means for spatially shifting and interpolating the views in accordance with each of a plurality of selected focal planes; and,
a means for summing the views spatially shifted in accordance with each of the focal planes to generate a slice image corresponding to each focal plane;
an image memory for storing the slice images; and
a video processor for converting selected portions of the slice images in the image memory into an appropriate format for display on a monitor.

2. An apparatus for imaging a region of interest of an object to generate a three dimensional image representation, the apparatus comprising:
a radiation source for sending a beam of penetrating radiation through the region of interest;
a moving system for cyclically moving the radiation source relative to the object during imaging through a path which passes closer and further from the object;
a flat panel detector stationarily mounted opposite the region of interest from the radiation source for detecting radiation after it has passed through the region of interest, the detector outputting a plurality of electronic views representative of detected radiation intensity variations across the detector in relation to a plurality of different positions of the radiation source relative to the region of interest; and,
a processor for receiving the plurality of electronic views from the detector, the processor including:
an image correction means for correcting blurring and distortion caused by variations in magnification of the plurality of electronic views as the radiation source moves closer and further from the object during imaging; and,
a means for generating a stack of slice images from the magnification corrected views to form the three dimensional image representation of the region of interest.

3. The apparatus as set forth in claim 2, wherein the processor further includes:
   a means for storing each of the plurality of electronic views;
   a means for shifting each of the plurality of electronic views such that radiation attenuation attributable to incremental elements within a selected focal plane, which is parallel to the detector, are displaced at a coherent location in each of the plurality of electronic views while radiation attenuation from incremental elements outside of the selected focal plane contribute to a plurality of locations on the detector; and,
   a view integration means for integrating the shifted views to generate a slice image in the stack of slice images in which data from the incremental elements within the selected focal plane is emphasized and data attributable to the incremental elements outside of the selected focal plane become blurred.

4. The apparatus as set forth in claim 3, wherein the processor includes a means for incrementing the selected focal plane such that the slice image of the stack of slice images is generated and further including a volumetric image memory for storing the stack of slice images.

5. The apparatus as set forth in claim 3 further including:
   an image correction means for reducing a contribution of the incremental elements outside of the selected focal plane in the slice image.

6. An apparatus for imaging a region of interest of an object to generate a three dimensional image representation, the apparatus comprising:
   an x-ray source for sending a beam of penetrating radiation through the region of interest of the object;
   a flat panel detector mounted stationarily relative to the object and the x-ray source for detecting radiation after it has passed through the region of interest of the object, the detector being disposed on an opposite side of the object from the radiation source, the detector outputting a plurality of electronic views representative of detected radiation intensity variations across the detector in relation to a plurality of different positions of the x-ray source relative to the object;
   a moving system for moving the x-ray source along an arcuate path such that the x-ray source remains a substantially fixed distance from the flat panel detector to minimize magnification effect; and,
   a processor for receiving and processing the plurality of electronic views from the detector to generate a stack of slice images parallel to the detector to form the three dimensional image representation of the region of interest.

7. The apparatus as set forth in claim 6, wherein:
   the moving system supports the x-ray source above the object; and,
   the flat panel detector is stationarily mounted below an object support device.

8. An apparatus for imaging a region of interest of an object to generate a three dimensional image representation, the apparatus comprising:
   a radiation source for sending a beam of penetrating radiation through the region of interest of the object;
   a moving system for supporting the radiation source below an object support device and for moving the radiation source relative to the object during imaging;
   a detector mounted above the object for detecting radiation after it has passed through the region of interest of the object, the detector being disposed on an opposite side of the object from the radiation source, the detector outputting a plurality of electronic views representative of detected radiation intensity variations across the detector in relation to a plurality of different positions of the radiation source relative to the object; and,
   a processor for receiving and processing the plurality of electronic views from the detector to generate a stack of slice images from an axis of the object which is parallel to the detector to form the three dimensional image representation of the region of interest.

9. An apparatus for imaging a region of interest of an object to generate a three dimensional image representation, the apparatus comprising:
   a radiation source for sending a beam of penetrating radiation through the region of interest of the object;
   a mechanism for moving the radiation source along a spiral trajectory such that the radiation beam passes through the region of interest from a multiplicity of angles and with a variety of radii;
   a flat panel detector for detecting radiation after it has passed through the region of interest of the object, the detector being disposed stationarily on an opposite side of the object from the radiation source, the detector outputting a plurality of electronic views representative of detected radiation intensity variations across the detector in relation to a plurality of different positions of the radiation source relative to the object; and,
   a processor for receiving and processing the plurality of electronic views from the detector to generate a stack of slice images to form the three dimensional image representation of the region of interest.

10. A method of generating three dimensional tomographic images of a region of interest of a patient, the method comprising:
   a) projecting penetrating radiation from a radiation source through the region of interest;
   b) receiving the radiation which has passed through the object on a stationary flat panel detector and converting the received radiation into electronic views indicative of variations in the received radiation across the detection plane;
   c) moving the radiation source to a plurality of positions relative to the region of interest such that radiation from the radiation source passing through each of a plurality of focal planes, which are parallel to the flat panel detector and within the region of interest, impinges upon spatially shifted offset portions of the flat panel detector;
   d) sampling the electronic views from the flat panel detector at each of a plurality of positions of the radiation source;
   e) spatially shifting the electronic views for a first selected focal plane, such that the radiation which passes through an incremental element on the first selected focal plane contributes to a common pixel of each spatially shifted electronic view;
   f) summing the spatially shifted electronic views such that the pixels of each spatially shifted electronic view corresponding to the incremental element on the first selected focal plane are summed to generate a first slice image taken through the first selected focal plane and such that radiation attenuation attributable to incremental elements of the region of interest which are off the first selected focal plane are distributed inconsistently among the pixels to form a background blur;

g) storing the first slice image in a volumetric image memory;

h) repeating steps (e), (f), and (g) with different spatial shifts corresponding to additional focal planes to generate additional slice images; and, i) storing the additional slice images in the volumetric image memory to form a three dimensional tomographic image.

11. The method as set forth in claim 10 further including:

selecting a plurality of focal planes and repeating the shifting and the summing of the electronic view to generate slice images, wherein each of the slice images corresponds to each of the plurality of focal planes.

12. The method as set forth in claim 11 further including:

storing each of the slice images; and, retrieving selected portions of the slice images and converting the retrieved selected portions into a display image.

13. The method as set forth in claim 10 further including:

filtering the slice images to remove blurred background attributable to the incremental elements of the region of interest off of the first selected focal plane.

14. A method of generating diagnostic images of a region of interest of an object, the method comprising:

projecting penetrating radiation from a radiation source through the region of interest;

receiving the radiation which has passed through the object on a radiation detection plane and converting the received radiation into electronic views indicative of variations in the received radiation across the detection plane;

cyclically moving the radiation source to a plurality of positions closer and further from the region of interest such that radiation from the radiation source passing through each of a plurality of focal planes, which are parallel to the detector plane and within the region of interest, impinge upon offset portions of the detector plane and such that there are variations in magnification among the electronic views;

scaling the electronic views to a common dimension;

shifting the electronic views for a first selected focal plane, such that the radiation which passes through an incremental element on the first selected focal plane contributes to a common pixel of the shifted and scaled electronic views;

shifting the electronic views for a second selected focal plane, such that the radiation which passes through an incremental element on the second selected focal plane contributes to a common pixel of the shifted and scaled electronic views; and, summing the shifted and scaled electronic views such that the pixels of each electronic view corresponding to the incremental element on the first selected focal plane are summed to generate a slice image taken through the first selected focal plane and the pixels of each electronic view corresponding to the incremental element on the second selected focal plane are summed to generate a slice image taken through the second selected focal plane such that radiation attenuation attributable to incremental elements of the region of interest which are off the first and second selected focal planes are distributed inconsistently among the pixels to form a background blur.

* * * * *